United States Patent [19]
Lehmberg et al.

[11] Patent Number: 5,952,023
[45] Date of Patent: *Sep. 14, 1999

[54] ENZYME EXTRACTION PROCESS FOR TEA

[75] Inventors: Gregg Lance Lehmberg, Somerset; Douglas Ashley Balentine, River Vale; Robert Steven Hang, North Bergen; Steven Alphonse Gobbo, Secaucus, all of N.J.

[73] Assignee: Lipton, Division of Conopco, Inc., Englewood Cliffs, N.J.

[*] Notice: This patent is subject to a terminal disclaimer.

[21] Appl. No.: 08/883,815

[22] Filed: Jun. 27, 1997

Related U.S. Application Data

[63] Continuation of application No. 08/596,930, Feb. 5, 1996, abandoned.

[51] Int. Cl.$^6$ ........................................................ A23F 3/00
[52] U.S. Cl. ................ 426/50; 426/49; 426/52; 426/590; 426/597
[58] Field of Search .................. 426/49, 50, 52, 426/590, 597

[56] References Cited

U.S. PATENT DOCUMENTS

| | | |
|---|---|---|
| 2,831,772 | 4/1958 | Herz . |
| 2,863,775 | 12/1958 | Perech . |
| 3,812,266 | 5/1974 | Sanderson et al. . |
| 3,959,497 | 5/1976 | Takino . |
| 4,051,264 | 9/1977 | Sanderson et al. . |
| 4,478,939 | 10/1984 | Adler-Nissen et al. . |
| 4,483,876 | 11/1984 | Petersen . |
| 4,639,375 | 1/1987 | Tsai . |
| 5,445,836 | 8/1995 | Agbo et al. . |

FOREIGN PATENT DOCUMENTS

| | | |
|---|---|---|
| 1249932 | 7/1969 | United Kingdom . |
| 1380135 | 2/1972 | United Kingdom . |
| 1413351 | 1/1973 | United Kingdom . |
| 1546508 | 3/1976 | United Kingdom . |

OTHER PUBLICATIONS

Sanderson & Coggon, ACS Symposium Series No. 47 pp. 12–26 (1977).
Roberts, J. Sci. Food Agric. 3 193–8 (1952).
Product Brochure NOVO, Celluclast® 1.5.L.
Product Brochure NOVO, Viscozyme™ L.

*Primary Examiner*—Leslie Wong
*Attorney, Agent, or Firm*—James J. Farrell

[57] ABSTRACT

An improved process for the preparation of acid stable instant tea. Enzymatic extraction of black tea leaf using an enzyme cocktail adjusted to a critical pH is employed. Black tea is extracted with water containing tannase and one or more cell wall digesting enzymes, such as cellulase, pectinase, hemicellulase or VISCOZYME at a selected pH. The resulting tea extract can then be pasteurized, polished and made into a finished beverage or concentrated and dried in the usual manner. As a result, natural tea products are obtained which have improved acid stability, good color and good clarity.

14 Claims, 1 Drawing Sheet

ENZYME EXTRACTION PROCESS FOR TEA

This is a continuation application of Ser. No. 08/596,930, filed Feb. 5, 1996, now abandoned.

FIELD OF THE INVENTION

The present invention relates to an improved process for obtaining instant tea and to the improved products thereby obtained. In particular, the invention relates to a method of treating black tea leaf with an enzyme cocktail including tannase and selected cell wall lysis enzymes such as cellulase, mascerase and carbohydrases, for example, VISCOZYME L obtainable from NOVO Industri A/S, Denmark, to produce instant tea which has improved acid stability with good cold water solubility, good clarity and tea color and which has a full complement of tea flavor. The improvement is in the pH of the enzyme solution used for the extraction process.

BACKGOUND OF THE INVENTION

Enzymatic treatment of tea leaves either continuously or batchwise for the production of instant teas offers many benefits for the resulting convenience beverage product. These include better acid stability, color, clarity, cold water solubility, flavor and higher yield. Continuous processing of tea leaf with enzymes is an economical method of providing the necessary operating conditions of time, temperature, enzyme concentration and water for the enzymes to be effective. The high throughput needed for commercial production is also accommodated by continuous processing with minimal complexity compared to batch operation.

The long contact times required for enzymes to be used effectively makes batch processing complex and requires a large capital investment in equipment to provide the residence time. Continuous, plug flow treatment reduces the amount and complexity of equipment needed to treat tea leaf with enzymes and allows for easy integration to downstream continuous extraction process equipment. Consistent, reproducible results is a further benefit of continuous treatment.

Black tea is usually prepared by subjecting freshly picked tea leaves to a series of processing conditions including the withering and rolling of freshly harvested leaves, followed by a fermentation step (enzymatic oxidation) during which much of the characteristic color, flavor and aroma of black tea are developed. The fermentation is halted after a suitable period of time by "firing" or drying the tea at temperatures ranging from about 65° C. to about 100° C. to inactivate the enzymes causing the fermentation. This completes the development of the flavor and color of the tea product. The extent of fermentation varies, in commercial practice, from black to various gradations between green and black. Partially fermented teas are known as "oolong" teas. Green teas are made by firing green tea before fermentation has taken place. Green, oolong, and black tea each provide a beverage having distinctive flavor and color characteristics.

When conventional teas are extracted with cold water for short periods of time (less than 15 minutes), the tea beverage produced has a low concentration of extractable tea solids, a very light color and almost no tea-like taste. Water at temperatures of about 100° C. is customarily employed by the prior art to obtain a satisfactory beverage.

Various procedures are known in the art for making cold water soluble instant tea powders by solubilizing tea cream obtained from black tea extracts, e.g., Herz, U.S. Pat. No. 2,831,772; Perech, U.S. Pat. No. 2,863,775. While each of these processes are successful to varying degrees in producing a cold water soluble instant tea powder, each has disadvantages. Most fail to provide a tea powder which, on reconstitution, gives a beverage having a natural flavor and color.

Sanderson et al. U.S. Pat. Nos. 3,812,266 and 4,051,264 employs tannase with green tea.

Tsai. U.S. Pat. No. 4,639,375 treats tea with a combination of tannase and one or more cell wall lysis enzymes but only prior to extraction.

There is a substantial body of literature on the role of enzymes in tea manufacture, which has been summarized in two review articles, Sanderson & Coggon, *ACS Symposium Series*, No. 47, 12–26 (1977); and Roberts, *J. Sci. Food Agric.*, 3, 193–8 (1952).

U.K. Patent 1,249,932, relates to a process for the solubilization of tea cream and to the preparation of water-soluble tea concentrates by the use of an appropriate enzyme, especially tannase.

U.K. Patent 1,380,135, describes the preparation of a cold water soluble instant tea powder containing solubilized tea cream. The process of the '135 specification involves either separating cold water-insoluble tea solids from the hot water extracted tea and treating them with tannase or treating the hot water extract of tea with tannase without separation.

U.K. Patent 1,413,351, relates to a process in which unfermented or green tea is contacted with tannase and is subsequently converted to black tea.

U.K. Patent 1,546,508, relates to a method of treating fresh green tea leaf with tannase.

U.S. Pat. No. 5,445,836 relates to a process for producing tea extract with reduced haze under refrigeration using tannase and glucose oxidase to treat decreamed tea extract.

U.S. Pat. No. 3,959,497, relates to enzymatic solubilization of tea cream by treating tea extract or tea cream with enzymes.

It is an object of this invention to provide an enzymatic extraction where the enzyme cocktail has been adjusted to a selected pH for the treatment of black tea leaf which produces a high quality natural product with good acid stability having haze values of a final black tea beverage of less than 50 as measured by a Hunter Colorimeter.

It is another object of this invention to provide an improved continuous process for enzymatic extraction of black tea leaf which produces a product having better acid stability, greater cold water solubility, better color and better clarity than conventional black tea extracts.

These and other objects of the invention will be evident from the following disclosure.

SUMMARY OF THE INVENTION

Black tea is obtained in the usual way and employed in the instant process. Black tea leaf can be used as received.

An enzyme cocktail containing tannase and selected cell wall lysis enzymes is prepared. It has been found that the pH of the enzyme cocktail which includes tannase in combination with the other enzymes is critical to obtain high tannase activity to result in a high yield of gallic acid. It is believed that the gallic acid content of the instant tea product is in part indicative of solubility with higher levels of gallic acid correlating to better solubility.

While not wishing to be bound by theory, it is nevertheless theorized that treatment of the tea leaves with the tannase and cell wall digesting enzymes leads to a soluble tea product with a unique biopolymer profile. Tannase results in increased gallic acid or gallic acid salt levels from modification of polyphenolic type biopolymers such as theaflavins and thearubigins. The cell wall digesting enzymes release and modify plant cell wall biopolymers, thus creating products which contribute to flavor and acid stability.

While it is known that certain tea polyphenols precipitate selected proteins particularly under acidic conditions below the isoelectric point of the proteins, the modification of the proteinaceous biopolymers present in tea leaves to a favorable profile as disclosed herein improves solubility.

The enzymes are fed to a black tea/water slurry in the extractor at low temperature to obtain a tea extract slurry. The enzymes can be combined into a cocktail with appropriate pH adjustment or can be fed to the extractor individually to limit the contact time between the enzymes. The tea extract slurry containing the enzymes is hot extracted to complete the extraction process and the tea leaf is separated from the tea extract. The tea extract is then pasteurized. This heat treatment deactivates the enzyme cocktail.

The separated or decanted tea extract may then be stripped if desired, to collect additional aroma.

The optionally stripped extract is then cooled and polished by centrifugation or other clarification methods such as filtration and the like. It has been found that during centrifugal polishing a selected tea solids content and a particular temperature are essential to produce a product of the desired color, clarity and acid stability.

After polishing the extract may then be concentrated and spray dried in the usual manner to a powdered instant tea or the extract can also be employed as a liquid or syrup when preparing tea based beverages.

About 5 to 20 parts and preferably 5 to 8 parts by weight of water based on the weight of tea leaf is heated to between about 70° F. and 145° F., preferably 120° F. to 140° F. The water is added to the tea leaf and an enzyme mixture consisting of any combination of tannase with the following: Carbonhydrases such as cellulase, pentinase and mascerase are metered continuously into the extractor. The pH of the tannase containing solution is adjusted to about 4 to 10 and preferably 5.5 or higher before contacting the tea. The extractor can be jacketed or insulated to aid in temperature control. The flow of tea leaf, water and enzymes through the extractor is preferably co-current. The length, diameter and flow rates of the system are such that they provide a minimum contact time of at least 20 minutes, preferably at least 60 minutes. The maximum is about 2 to 5 hours or more, depending upon the degree of extraction desired balanced against economics.

The resulting slurry can be separated into extracted tea leaf and extract or be sent on for further batch or continuous extraction. The extract is then optionally aroma stripped by conventional means and adjusted to the desired solids level, cooled and centrifuged to remove insoluble material. The extract is optionally batched into a finished beverage or, if desired, can be concentrated and/or dried for example spray dried.

The color and clarity of the resulting product is significantly improved if the centrifugation is done on an extract of about 4.0 wt. % to 10 wt. % tea solids.

There are several product advantages to the improved instant tea process. Acid stability is one advantage. This refers to the tendency for solids to precipitate or floc out of solution, especially in acid systems. Other benefits are improved color, clarity, cold water solubility, flavor, and extraction yield.

Acid stability as referred to herein may be measured by two different methods. Method 1 is employed to determine the acid stability of a finished product prepared from tea powder, flavor, citric acid, water and optionally sweetener, e.g., sugar aspartame and the like. The water employed preferably has a hardness of 170 ppm. The finished product is visually inspected for precipitated floc. Color and clarity are measured using a Hunter Colorimeter with a 4 cm sample cell. A haze value of less than about 50 is acceptable. The product is then stored at about 40° F. for 48 hours. At the end of this period the product is again observed for flocculated particles or precipitation and again measured for color and clarity. The product is acid stable if there is no floc or precipitation and there is no substantial change in haze value and thus the haze still must remain less than about 50. The tea extract used to prepare to powder is, in like manner, acid stable. The Hunter Colorimeter employed is a Hunter Lab Color Quest System with a Hunter Lab DP-9000 data module.

In method 2 an instant tea sample is made up to a product strength of 0.17% w/v in water, in a buffer solution at pH 2.5. To pass the visual observations the sample should remain clear without any sign of precipitate formation when dissolved in pH 2.5 buffer after 24 hours.

Along with visual observations, readings for haze and color using a Hunter Colorimeter are also recorded.

Equipment

Hunter Colorimeter with 4 cm or 5 cm cells;
Tapered graduated tubes—10 ml.
Method 2

Phosphate/Citric Acid Buffers

I. Stock Solutions.
   A. 0.4M di-Sodium hydrogen orthophosphate is prepared in deionized water.
   B. 0.2M Citric acid is prepared in deionized water.
II. Dilute Working Buffer Solutions. pH 2.50 Buffer. 85 ml of phosphate solution A is mixed with 915 ml citric solution B.

Procedure 0.17 g of instant tea powder is added to a conical flask. 50 ml of deionized water is then added to the flask and the flask is shaken to dissolve the tea powder. 50 ml of pH 2.50 buffer solution is added to the flask, the contents are mixed and then without undue delay the haze and color (L values) are measured. After allowing the extract to stand overnight, the extract in the graduated tube is examined and any signs of precipitate formation either suspended or settled is noted. Further haze and color measurements are performed to confirm a good batch of product.

To pass the visual observations the sample should remain clear without any sign of precipitate formation when dissolved in pH 2.5 buffer after 24 hours.

DESCRIPTION OF THE PREFERRED EMBODIMENT

Figure 1:
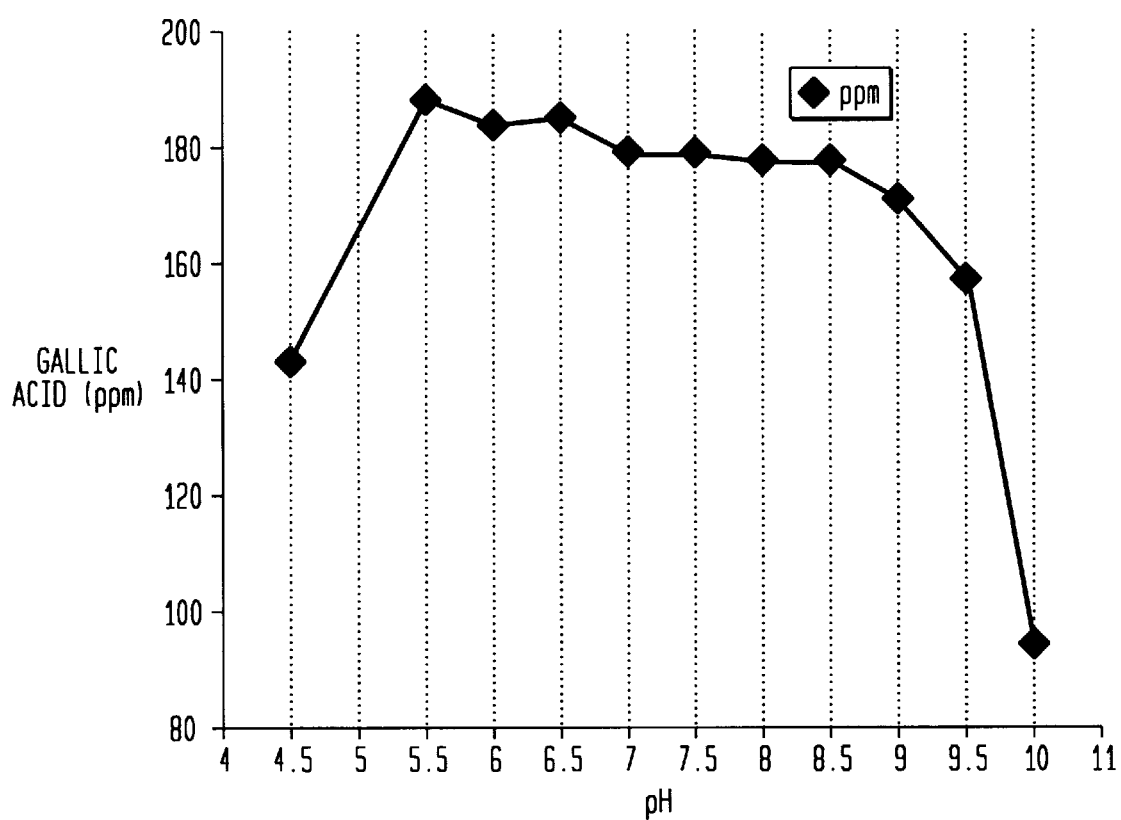
FIG. 1 shows the effect of pH on gallic acid release over time.

Aroma Stripping 100 lb. of tea leaf is fed into a Hopper. The leaf is then fed into an Aroma Stripper. The leaf in the Stripper is then steam stripped to collect fractions of tea volatiles or aroma. The steam stripped aroma leaves the vessel and is condensed and collected. Other methods of aroma collection are also acceptable. After stripping, the tea leaf is metered into the emzyme extractor.

Enzyme Preparation

The enzyme cocktail is prepared by mixing selected cell wall digesting enzymes such as CELLUCLAST and VISCOZYME obtainable from NOVO in selected ratios such as 1 part Celluclast to 2 parts VISCOZYME together with various enzyme stabilizing agents such as sorbitol and the like in water. Tannase may also be prepared by adding the enzyme to water, but the tannase may also be added as a dry powder. The enzymes are mixed together and their pH is adjusted to about 4 to 10, more preferably 5.5 or above. Preferably a pH of 6 or above so long as the enzyme is not denatured. The cell wall digesting enzyme mixture has its pH adjusted to 5.5 or above prior to dissolving or adding the tannase into the enzyme cocktail, so long as the combination has a pH of about 5.5 or above and preferably about 6.0 or above before addition to the tea leaf. It is also possible to introduce the enzymes separately into the extractor.

The enzyme batch contains about 340 grams of the cell wall digesting enzymes and contains about 3.8 grams of the tannase on the carrier. The temperature of the enzyme solution is controlled to about 35° F. to 55° F. and preferably about 45° F. to insure high activity. The combination or cocktail is then added to the extractor at a rate of about 3.4 g per minute.

The addition of the enzyme solution at the critical pH to the extractor affects the carbohydrate composition, gallic acid concentration, the acid stability and the cold water solubility and yield. The preferred conditions of extraction are as follows:

Temperature in the Extractor about 70° F. to 145° F. and preferably about 120° F. to about 140° F.

Enzyme Temperature in Prep Tank (target 45° F.)

Enzyme Feed Rate target 3.4 gm./min.

Leaf Feed Rate target 60 lbs./hr.

Water Feed Rate 5.0 to 8.0 lb/min.

Enzyme Extraction Operation

The tea leaf is fed to the enzyme extractor from the aroma stripper together with fresh water and enzyme solution. All three components flow co-currently through the extractor. The extractor is preferably temperature controlled by jacketing or the like.

The enzyme extractor preferably provides about 20 minutes to about 2 to 5 hours or more of residence time for the enzyme solution to be in contact with the leaf. Temperature control is important to maximize the effect of the enzymes.

Operating Parameters for the Enzyme Extractor

The following table highlights the preferred operating parameters:

| Operating Parameter | Specification |
| --- | --- |
| Leaf Feed Rate | 60 lb/hr |
| Feedwater Rate | 0.6 to 0.95 gallons/min. |
| Enzyme Feed Rate | 3.4 gm/min |
| Slurry Temp. in Troughs | 120–140° F. |

Enzyme Feed Rate

This is critical to control the finished product quality. Lower rates will result in high haze due to under-treating of the tea leaf. Higher rates cause an undue waste of the enzyme.

Slurry Temperature

The enzymes function best within a specific temperature range. Temperatures outside of that range (either higher or lower) will result in under-treatment of leaf with enzymes and, therefore, higher hazes and higher polishing losses.

The residence time in the extractor is also important. Slower speeds will result in leaf movement problems and backups in the extractor. Higher speeds will result in insufficient contact time with enzymes and high haze due to under-treatment.

High Temperature Extraction

Following the enzyme extraction step, the leaf slurry is preferably fed into a high temperature extractor at a temperature of about 180° F. to 200° F preferably 190° F. This completes the extraction of the leaf. The ratio of tea leaf to water in this extraction is about 4 parts to 10 parts water to 1 part leaf.

Pasteurization

Decanted extract from the hot extraction step is pumped at about 2% to 5% tea solids to the Pasteurizer. Pasteurization is accomplished by raising the temperature of the extract to a minimum of about 190° F. The hot extract is then held for about one to ten minutes of residence time to destroy any microorganisms that might be present in the extract. The pasteurization step also denatures the enzymes and stops their activity.

The pasteurized extract is then again stripped of aroma if desired and concentrated to the appropriate level for centrifugal polishing.

Polisher Operation

The feed solids concentration and temperature of the extract being polished has been determined to be critical to achieving good quality product. The concentrated pasteurized extract is best polished at a tea solids concentration of about 4% to about 10%.

The extract temperature should be about 120° F. or less, preferably about 55° F. to 70° F. The extract is fed to a centrifuge where it is spun for nominally 2 minutes at approximately 8,000 times gravity. The sludge is disposed of and the polished extract retained for formulating into finished beverages, concentration and/or drying.

Evaporation

The polished extract may then be concentrated by evaporation or other methods if desired.

Aroma Addition

Tea concentrate from the evaporation process is collected and aroma or volatiles previously collected may be added if desired.

Drying

The concentrated extract is then dried if a tea powder is being produced. The extract can also be diluted and used directly if a ready to drink beverage is desired.

There are many variables that affect product quality and yield at the drying step. Drying processes are well known in the art.

In a preferred process of this invention, black tea leaf is mixed with an enzyme cocktail at a pH of about 5.5 or above preferably 6 or above and weight ratio of from about 0.005 to 0.010 parts of enzyme to 1 part preferably 0.007 to 0.008 parts enzyme per part tea leaf. The enzyme solution contains tannase and one or more cell wall lysis enzymes. Preferably, the enzyme solution contains from about 0.5 to 10 units of tannase activity per gram of black tea, from about 2.5 to 5.0 NCU of cellulase and about 0.33 to 0.66 FBG of carbohydrase, per gram of black tea. The tea is extracted with the enzymes at a temperature of from about 70° F. to about 145° C. for from about 20 minutes to about 5 hours or more. After extraction the enzymes are inactivated by heating to a temperature greater than 150° F. and preferably about 190° F. or above and the tea is then ready for further processing in accordance with the invention.

Enzyme Solution

By "cell wall-digesting enzyme" herein is meant an enzyme which breaks down one or more tea cell wall constituents to simpler materials and thus reduces the structural integrity or increases the permeability of the cell wall. Plant cell walls are composed primarily of cellulose, but contain lesser amounts of proteins, hemicellulose, pectins, and lipids. Accordingly, cell wall digestive enzymes include carbohydrase such as cellulase, hemicellulase, pectinase and dextranase; protease, lysozyme and lipases. For example, Novo Industries U.S. Pat. Nos. 4,478,939 and 4,483,876 describe SPS-ase activity.

The tannase, which is used in this invention, is known to hydrolyze galloyl esters. The enzyme is an elaboration product of the growth of certain molds belonging to the genera Aspergillus and Penicillium. *Aspergillus flavus* grown on a medium containing tannic acid as a sole carbon source provides tannase in substantial amounts. Two other specific strains of microorganisms known to produce substantial quantities of tannase are *Aspergillus oryzae*, ATCC No. 9362, and *Aspergillus niger*, ATCC No. 16888. One suitable preparation of tannase enzyme is available commercially from the Enzyme Development Corporation. Yet another is available from Kikkoman. The other cell wall digesting enzymes, such as cellulase, papain, pectinase, and hemicellulase can be obtained from similar commercial enzyme sources. An example of the measurement of tannase activity is given below.

Tannic acid is hydrolyzed in the presence of tannase to gallic acid and a sugar moiety. The hydrolysis of tannic acid results in a reduction of UV absorbance at 310 nm. Tannase activity is therefore determined from the change in absorbance and is defined as the amount of enzyme which hydrolyses 1 micromole of ester bond in tannic acid per minute under the conditions described below.

Reagents and Solutions (1) Citrate Buffer (0.05M, pH 5.5)

Dissolve 9.6 grams of anhydrous citric acid in 800 ml of water. Adjust pH with NaOH (50%) to 5.5 and dilute to 1000 ml with deionized water.

(2) Cell Wall Digesting Enzyme Solution (33.0%)

This solution is a mixture of VISCOZYME L and CELLUCLAST that have been blended in a ratio of 2:1. The mixture serves as the solvent, stabilizer and blank for the tannase analysis. The solution is prepared on a W/V basis with deionized water. The pH is adjusted with sodium hydroxide to 5.5.

(3) Substrate Solution (Tannic Acid, 0.350% W/V)

The substrate is prepared just before use by dissolving 175 mg of tannic acid in citrate buffer (1) which is then made up to a volume of 50 ml using a volumetric flask.

(4) Ethanol Solution (90%)

100 ml of deionized water is added to a 1000 ml volumetric and the volume is brought to 1000 ml with ethanol.

(5) Tannase Solution (Approx. 2.6–29 units/ml.)

The tannase solution is prepared by dissolving 0.1000 grams of tannase in the cell wall digesting enzyme solution (2) W/V to produce a solution that contains 1.000 mg/ml tannase. 1.0 ml of tannase solution is diluted with 18 ml of citrate buffer (1). This brings the tannase into the required activity range for U.V. analysis The blank is prepared in the same way by mixing 1.0 ml of Novoferm 91 (2) solution with 18 ml of citrate buffer (1).

Stability of Solutions: Citrate buffer (1) when stored at 4° C. is stable as long as no microbial action occurs. The cell wall digesting enzyme solution (2) and substrate solution (3) must be freshly prepared and protected from light. Ethanol solution (4) may be stored at room temperature. Enzyme solution (5) may be stored for several hours at about 0°–4° C. after preparation.

Procedure

A. The substrate solution (3) is transferred to a flask and warmed in a water bath at 30° C. for 15 minutes before starting the enzyme reaction.

B. 1.0 ml aliquots of enzyme solution (5) are transferred into test tubes (10 ml). For blank test samples the cell wall digesting enzyme blank solution as specified in (2) is used. All test tubes are warmed in a water bath at 30° C. for 5 minutes before starting the enzyme reaction.

C. The test/reaction is begun by adding 4.0 ml) of substrate solution (3) to each test tube (at 30 second intervals) and incubated for 15 minutes at 30° C.

D. The reaction is quenched in flasks for each test sample by adding ethanol solution (4) to each flask. At the end of the reaction time, which should be 15 minutes for each test sample, 952 ul of sample is transferred to the ethanol stop solution and mixed thoroughly. The sample is diluted to volume with additional ethanol solution (4) and mixed.

E. The absorbance of each solution is measured at 310 nm using water as a reference.

Calculations (1) The absorbance measurements that were taken for the samples and blanks are averaged.

(2) Tannase activity may then be calculated from the following equation:

Tannase Activity (Units/gram)=$\Delta A * 150670$

The cell wall digesting enzymes may be cellulase such as CELLUCLAST 1.5 L obtainable from Novo Industries. This material is prepared by fermentation of a selected strain of *Trichoderma reesei*. This cellulase catalyzes the breakdown of cellulose into glucose, cellobiose and higher glucose polymers. CELLUCLAST 1.5 L has 1,500 NCU/g.

One Novo Cellulase Unit (NCU) is the amount of enzyme which, under standard conditions, degrades CMC to reducing carbohydrates with a reduction power corresponding to 1 $\mu$mol glucose per minute.

| Standard Conditions | |
| --- | --- |
| Substrate | CMC (Hercules 7 LFD) |
| Temperature | 40° C. |
| pH | 4.8 |
| Reaction time | 20 minutes |

Another cell wall digesting enzyme is VISCOZYME L obtainable from Novo. VISCOZYME 120 L is a multi-enzyme complex containing a wide range of carbohydrases including arabinase, cellulase, β-glucanase, hemicellulase and xylanase. The enzyme also has activity against the branched pectin like substances found in the soy bean cell walls.

The enzyme preparation is produced from a selected strain of the Aspergillus group. The product has an enzyme activity of 120 FBG/ml. (Fungal β Gluconase). The analytical method is available from Novo.

It is found that the pH of the mixed enzyme cocktail particularly containing Tannase is critical in obtaining high tannase activity. The combination of cell wall digesting enzymes such as Celluclast and VISCOZYME has a pH of about 4.5 and this may be adjusted up to 10. Preferably the pH is 5.0 to 6.5 and usually 6 or above to provide higher tannase activity and stability when the tannase is mixed in with the other enzymes. Table 1 below provides an analysis of varying pH and % gallic acid.

TABLE 1

Effect of pH on Gallic Acid Release for a Variety of Enzyme Preparations

| Experiment # | % Solids | Gallic Acid ppm | Gallic Acid % | pH | Water Quality |
| --- | --- | --- | --- | --- | --- |
| 1 | 0.397 | 138.6 | 3.49 | 4.6 | Tap water |
| 2 | 0.398 | 162.9 | 4.09 | 5.4 | Tap water |
| 3 | 0.395 | 141.2 | 3.57 | 4.5 | None |
| 4 | 0.399 | 168.2 | 4.22 | 5.4 | None |
| 5 | 0.363 | 176 | 4.84 | 5.4 | Deionized |
| 6 | 0.38 | 131.9 | 3.47 | 4.5 | Deionized |
| 7 | 0.39 | 136.1 | 3.49 | 5.5 | Deionized |
| 8 | 0.386 | 159.1 | 4.09 | 6 | Tap water |
| 9 | 0.418 | 178.7 | 4.28 | 5.3 | Tap water |
| 10 | 0.418 | 179.4 | 4.3 | 5.3 | Deionized |
| 11 | 0.411 | 166.7 | 4.06 | 4.5 | Deionized |
| 12 | 0.402 | 138.2 | 3.44 | 4.6 | Tap water |
| 13 | 0.418 | 151.3 | 3.62 | 4.5 | Deionized |
| 14 | 0.416 | 154.8 | 3.72 | 4.5 | None |
| 15 | 0.424 | 156.8 | 3.7 | 4.5 | Deionized |
| 16 | 0.411 | 155.5 | 3.78 | 4.5 | None |
| 17 | 0.414 | 136.7 | 3.3 | 4.5 | Deionized |
| 18 | 0.403 | 144.9 | 3.6 | 4.9 | Deionized |
| 19 | 0.413 | 173.4 | 4.2 | 5.5 | Deionized |
| 20 | 0.416 | 178.1 | 4.28 | 5.9 | Deionized |
| 21 | 0.416 | 172.4 | 4.15 | 6.4 | Deionized |
| 22 | 0.359 | 45.6 | 1.27 | | |

The percent solids is the total tea solids. The water is either tap water, deionized water or none. The pH is self explanatory. Clearly the difference in adjusting the pH appropriately results in dramatic differences in the % of gallic acid.

The graph in FIG. 1 shows the effect of pH on gallic acid release over time. The % gallic acid is based on total tea solids and was measured by HPLC.

In addition to the pH of the enzyme treating solution being extremely important it is also found that the polishing/cooling step is very important. The amount of solids in the extract should be from about 3.5% to about 20%, preferably from 4% to 10% in order to achieve good color and clarity.

The temperature to which the extract is cooled is also important. The temperature should be less than about 120° F. and preferably about 55° F. to 70° F.

Although the invention has been described in detail with respect to preferred embodiments thereof, variations and modifications will be readily apparent to those skilled in the art without departing from the spirit and scope of the invention as set forth in the claims.

What is claimed is:

1. A process for producing a soluble black tea product by enzymatic extraction, said product upon being reconstituted into an acidic beverage, remaining stable, comprising the steps of:

(1) co-extracting fermented black tea leaf with water and an enzyme cocktail having a pH of about 4 to about 10 comprising tannase and one or more cell wall-digesting enzyme which break down one or more tea cell wall constituents to simpler materials;

(2) inactivating the enzymes by heating; and (3) clarifying the extract;

whereby said acidic beverage remains flocculate-free for 48 hours at 40° F. and has a haze value of less than about 50.

2. A process according to claim 1, wherein the extraction takes place for from about 20 minutes to about 5 hours.

3. A process according to claim 1, wherein the enzyme solution pH is about 5 to 6.5.

4. A process according to claim 1, wherein the cell wall-digesting enzyme is a member selected from the group consisting of cellulase, hemicellulase, pectinase, dextranase, lysozyme, lipase, and mixtures thereof.

5. A process according to claim 1, wherein the enzyme solution contains from about 0.5 to about 10 units of tannase per gram of tea leaf, wherein one unit is the amount of enzyme which hydrolyses one micromole of ester bond in 0.35% tannic acid in 0.1 m. citrate buffer having a pH of 5.5 in one minute at 30° C.

6. A process for producing tea extract by extracting said tea with an enzyme cocktail consisting essentially of tannase, and a cell wall digesting enzyme selected from the group consisting of cellulase, hemicellulase, pectinase, dextranase, protease, lysozyme, lipase and mixtures thereof at a pH of about 5.0 to 6.5 for about 45 minutes at a temperature of about 140° F.

7. A process as defined in claim 1, wherein the ratio of tannase activity per gram of tea leaf is about 0.5 to 10.

8. A process as defined in claim 1, wherein the ratio of cell wall digesting enzymes to tea leaf is about 25 to 5.0 NCU of cellulose and 0.33 to 0.66 FBG of a multi enzyme complex containing a wide range of carbohydrases derived from aspergillus (carbohydrase).

9. A process according to claim 1, wherein said extract is dried to form a powder.

10. A process according to claim 1, wherein said extract is reconstituted to form an acidic beverage.

11. A process according to claim 1, wherein said extract is concentrated to form a syrup.

12. A continuous process for producing a soluble black tea product by enzymatic extraction, said product upon being reconstituted into an acidic beverage, remaining stable, comprising the steps of:

(1) continuously co-extracting fermented black tea leaf with water and an enzyme cocktail having a pH of about 4 to about 10 comprising tannase and one or more cell wall-digesting enzyme which break down one or more tea cell wall constituents to simpler materials;

(2) inactivating the enzymes by heating; and (3) clarifying the extract;

whereby said acidic beverage remains flocculate-free for 48 hours at 40° F. and has a haze value of less than about 50.

13. A tea product comprising tea solids prepared from black tea leaf which has been extracted by aqueous treatment with tannase and at least one cell wall-digesting enzyme at a pH of about 5.0 to 6.5 and which, when formulated into a final product having a percent concentration of said tea solids of about 0.05% to 1.0%, does not form haze for 48 hours at 40° F. and remains free of precipitate.

14. An aqueous based black tea beverage having 0.01 to 1.0% tea solids; 0 to 15% of a sweetener, flavorants, an acidulant to a pH of 4.5 or less and no added pectin other than natural tea pectins;

said beverage being free of any substantial haze when stored for 48 hours at 40° F.;

said beverage having been produced from a black tea extract obtained by aqueous enzymatic extraction with an enzyme mixture comprising tannase, cellulase and carbohydrase with enzyme solution having a pH of 4 to 10;

said beverage having at least .00025% to .025% of gallic acid or salts and having a biopolymer profile having reduced levels of protein and unique carbohydrate biopolymer profiles as compared with tea extracted only with water.

* * * * *